United States Patent

Hohaus et al.

Patent Number: 5,410,214
Date of Patent: Apr. 25, 1995

[54] ELECTRIC LAMP

[75] Inventors: Karl-Heinz Hohaus, Linnich, Germany; Hendrikus A. M. Van Dulmen; Joseph A. Meertens, both of Eindhoven, Netherlands

[73] Assignee: U.S. Phillips Corporation, New York, N.Y.

[21] Appl. No.: 227,229

[22] Filed: Apr. 13, 1994

Related U.S. Application Data

[63] Continuation of Ser. No. 822,494, Jan. 17, 1992, abandoned.

[30] Foreign Application Priority Data

Jan. 28, 1991 [NL] Netherlands .......................... 9100137

[51] Int. Cl.⁶ .............................................. H01J 5/50
[52] U.S. Cl. .................................. 313/318.1; 313/624; 313/625; 439/611
[58] Field of Search ............... 313/318, 624, 625, 274, 313/287, 331; 439/611, 612, 613

[56] References Cited

U.S. PATENT DOCUMENTS

| | | |
|---|---|---|
| 3,001096 | 9/1961 | Mosby . |
| 4,011,480 | 3/1977 | Jacobs et al. .................. 313/625 X |
| 4,918,355 | 4/1990 | Morris et al. ...................... 313/318 |
| 4,928,210 | 5/1990 | Hayakawa et al. ................ 313/318 |
| 4,970,428 | 11/1990 | Hayakawa et al. ................ 313/318 |
| 5,130,604 | 7/1992 | Franks, Jr. et al. ................ 313/318 |
| 5,241,239 | 8/1995 | Rao ................................. 313/624 X |

FOREIGN PATENT DOCUMENTS

| | | |
|---|---|---|
| 828294 | 11/1969 | Canada . |
| 0000480 | 1/1979 | Japan . |
| 2062957 | 5/1981 | United Kingdom . |

Primary Examiner—Donald J. Yusko
Assistant Examiner—N. D. Patel
Attorney, Agent, or Firm—Robert J. Kraus

[57] ABSTRACT

The electric lamp has a lamp vessel (1) having seals (4, 5) onto which respective bases (20, 21) are secured. Each base comprises a cylindrical insulator body (22) in a free end of which a contact member (30) is accommodated, having a contact face (31) and a protruding portion (33) which has a connection area (32) to which a current supply conductor (8) of the lamp is secured. The contact member (30) is a body made from metal foil.

20 Claims, 4 Drawing Sheets

ELECTRIC LAMP

This is a continuation of prior application Ser. No. 07/822,494, filed on 17 JAN. 1992, now abandoned.

BACKGROUND OF THE INVENTION

The invention relates to an electric lamp comprising a lamp vessel which is closed in a vacuumtight manner, in which an electric element is arranged, and which has a first and a second seal. Current supply conductors are connected to the electric element and issue from the lamp vessel to the exterior through the first and second seal, respectively.

Lamps caps fastened to the first and second seal, respectively, each comprise a cylindrical insulator body having a centreline. In a free end of each body a contact member is accommodated which has a contact face and a protruding portion with a connection area where a current supply conductor is fixed.

Such an electric lamp is known from U.S. Pat. No. 3,001,096.

The contact members therein consist of solid nickel bodies. A disadvantage of this is that the contact members are difficult to manufacture by means of operations such as pressing and cold deformation, and that machining operations such as milling, drilling and grinding may be necessary.

An electric lamp is known from CA-828 294 in which the contact member is a disc of metal plating against which the current supply conductor is fastened with solder in a butt joint. A disadvantage of this lamp is the use of solder, both because of the long process time in making the joint and because of the low heat resistance of this joint. A welded joint, however, would involve the risk of the contact face having a deformation owing to welding.

SUMMARY OF THE INVENTION

The invention has for its object to provide an electric lamp of the kind described in the opening paragraph which has improved contact members.

According to the invention, this object is achieved in a lamp of the kind described in the opening paragraph in that the contact member is a body formed from metal foil with a cylindrical flanged rim at the contact face, which rim supports the connection area.

The lamp according to the invention has the advantage that its contact members can be shaped in a deep-drawing process and that the connection area may have various shapes.

The contact members may consist of, for example, nickel, nickel-plated CrCu, or nickel-plated CuZn. In the case of nickel-plated contact members, nickel-plating may be realised before or after they have been shaped.

In a favourable embodiment, the cylindrical flanged rim has one or more, for example, two tongues as the connection area(s). Such a tongue may be bent away from the cylindrical rim and extend, for example, along the contact face. A current supply conductor may then be fastened by means of, for example, a butt weld. The tongue may alternatively have an end portion as the connection area, extending along the centreline of the insulator body, e.g. of ceramic. A current supply conductor may then be fastened laterally to this end portion. Resistance welding or laser welding, for example, are suitable for this purpose. Alternatively, the conductor may be clamped or, if the lamp has a comparatively low operating temperature, soldered.

It may be favourable if the current supply conductor is a U-shaped bent wire, or is obtained therefrom by separating the bend. The contact member may then be connected to the current supply conductor in two spots situated laterally next to one another. The contact member may for that purpose have two separate connection areas.

In another embodiment, the contact member has a strip formed from the cylindrical flanged rim which is created by an incision transverse to the centreline and which is bent towards this centreline to form the connection area. The strip may be folded in order to form a discrete location for a current supply conductor in a fold. Two such strips may alternatively be present in lamps having a current conductor with parallel portions, one for each portion.

The electric element of the lamp is of no importance for the principle of the invention. It may be an incandescent body, or a pair of electrodes, possibly in an inner envelope.

BRIEF DESCRIPTION OF THE DRAWING

This and other aspects of the lamp according to the invention are shown in the drawing figures, in which.

DESCRIPTION OF THE PREFERRED EMBODIMENTS

Figure 1:
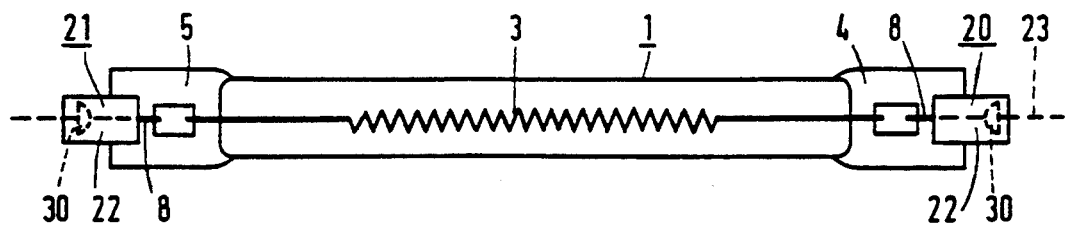
FIG. 1 shows a lamp in side elevation.

In FIG. 1, the electric lamp has a lamp vessel 1 which is closed in a vacuumtight manner and in which an incandescent body 3 is positioned as the electric element. The lamp vessel 1 has a first and a second seal 4, 5 through which current supply conductors 8 are passed from the incandescent body 3 to the exterior.

Lamp caps 20, 21 are fastened to the first and the second seal, respectively, for example with cement, such as lamp cement.

The lamp caps 20, 21 each have a cylindrical insulator body 22, e.g. of ceramic, which has a centreline 23, in a free end of which body a contact member 30 is accommodated. This member has a contact face 31 (FIGS. 2, 3) in order to effect an electrical connection with a lampholder through the open free end of the insulator body, and a protruding portion 33 with a connection area 32 to which the current supply conductor 8 is fastened.

The contact member 30 is a body formed from metal foil and having as a protruding portion a cylindrical ranged rim 33 at the contact face 31 which carries the fastening area 32.

Figure 2:
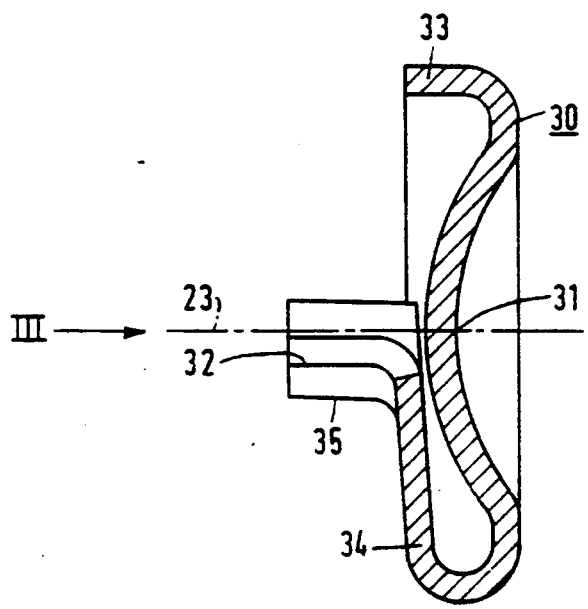
FIG. 2 shows an embodiment of a contact member in longitudinal section.
Figure 3:
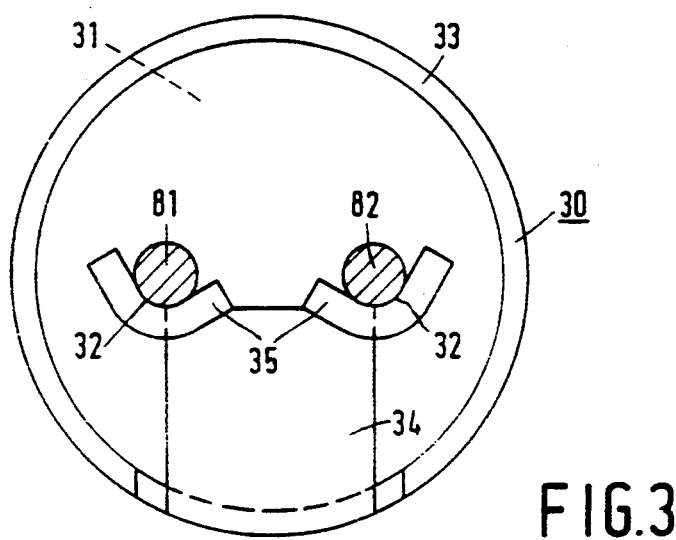
FIG. 3 shows the contact member of FIG. 2 taken on the line III.

The contact member 30 in FIGS. 2 and 3 has a concave, spherical contact face 31.

The ranged rim 33 has a tongue 34 which extends along the contact face 31 and which has an end portion 35 which runs alongside the centreline 23 and comprises the connection area 32.

The end portion 35 is split and has two concave curved connection areas 32 as predetermined seats on which parallel portions 81, 82 of a current supply conductor are fastened, for example, by laser welding.

Figure 4:
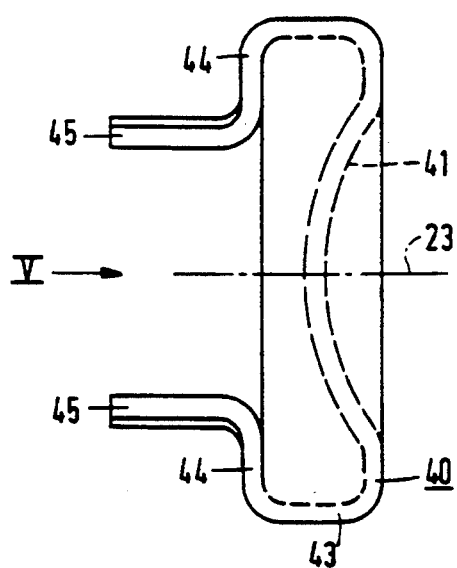
FIG. 4 is a side elevation of an alternative embodiment of a contact member.
Figure 5:
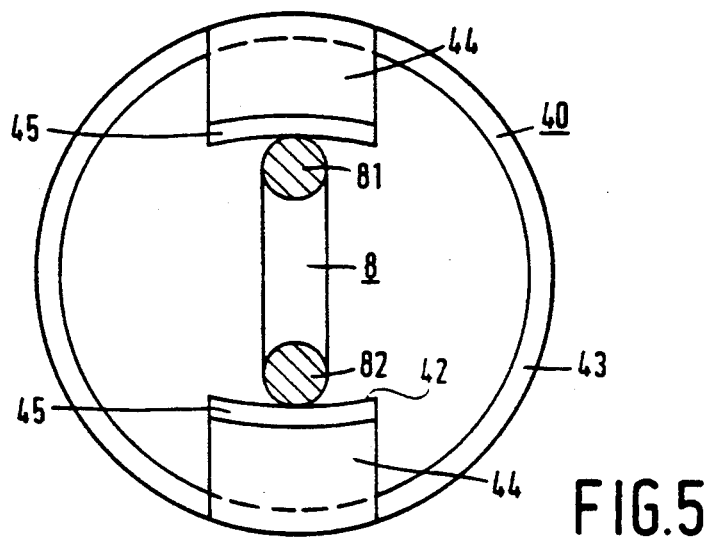
FIG. 5 shows the contact member of FIG. 4 taken on the line V.

In FIGS. 4, 5, corresponding parts of the contact member have reference numerals which are 10 higher than those in FIGS. 2, 3. The member has two tongues 44 with concave end portions 45 which face one another.

A current supply conductor 8 is brought between them and, owing to a relative rotation, takes up a position between these end portions 45 where the interspacing of these end portions corresponds to the external dimension of the U-shaped current supply conductor 8.

Figure 6:
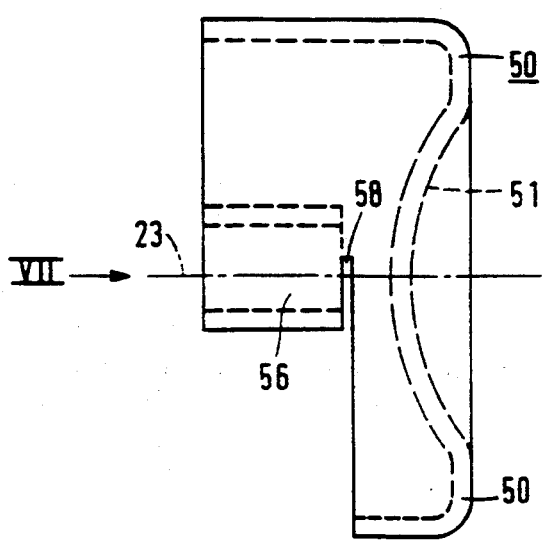
FIG. 6 is a side elevation of a further embodiment.
Figure 7:
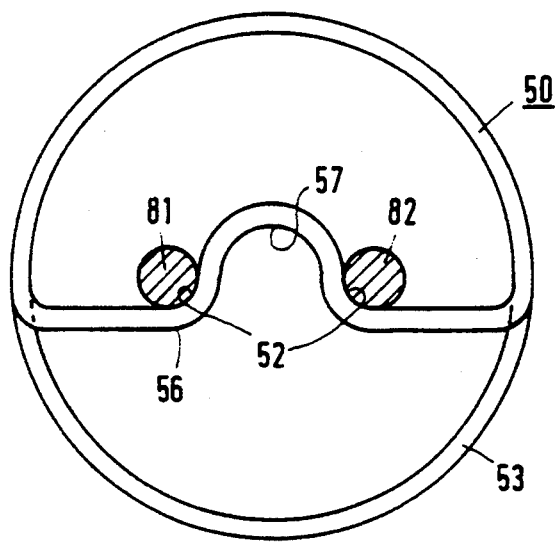
FIG. 7 shows the embodiment of FIG. 6 taken on the line VII.

In FIGS. 6, 7, the contact member 50 has a contact face 51 with a cylindrical flanged rim 53 from which a strip 56 is formed by an incision 58 transverse to the centreline 23, which strip is bent towards the centreline 23 to form the connection area 52. The strip has a bend 57 in order to form discrete connection areas 52 for current supply conductor portions 81, 82.

Figure 8:
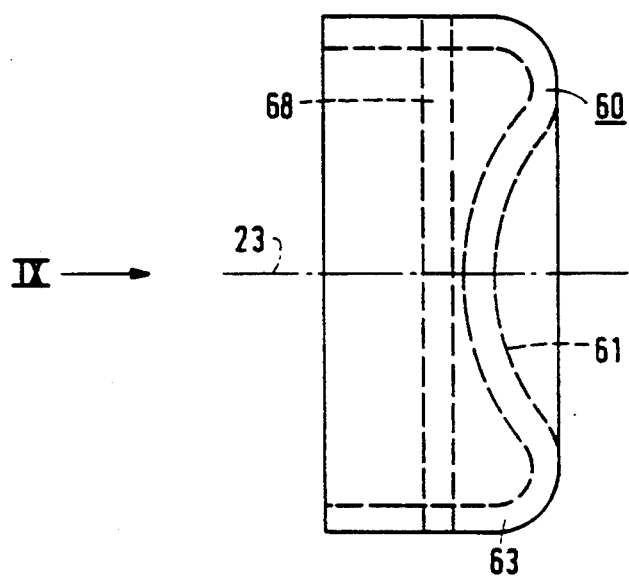
FIGS. 8 and 9 show a modification of FIGS. 6 and 7.
Figure 9:
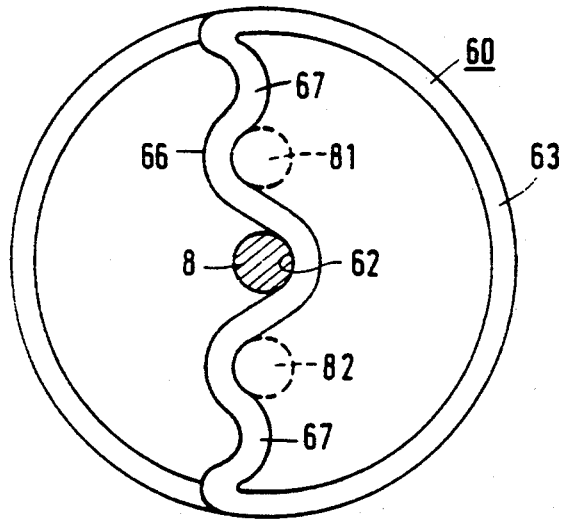

FIGS. 8, 9 show a modification with reference numerals which are 10 higher than those in FIGS. 6, 7. The strip 66 has bends 67 of such a nature that a discrete connection area for a current supply conductor is created, but also for parallel portions 81, 82.

Figure 10:
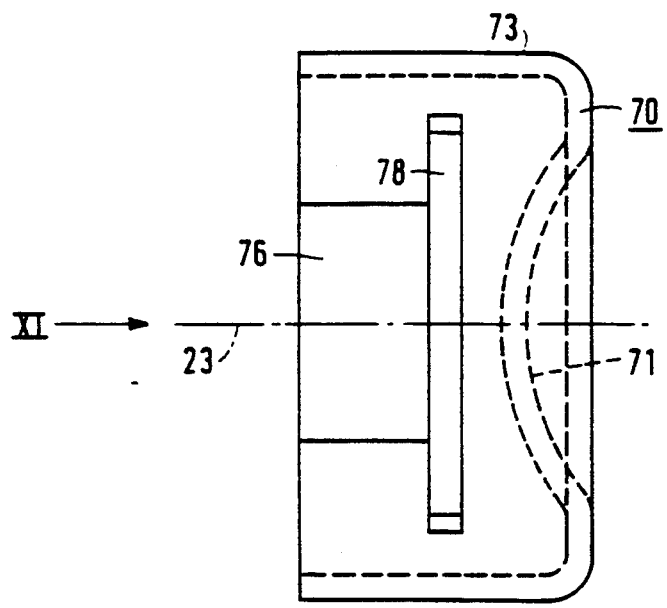
FIG. 10 shows a next embodiment in side elevation.
Figure 11:
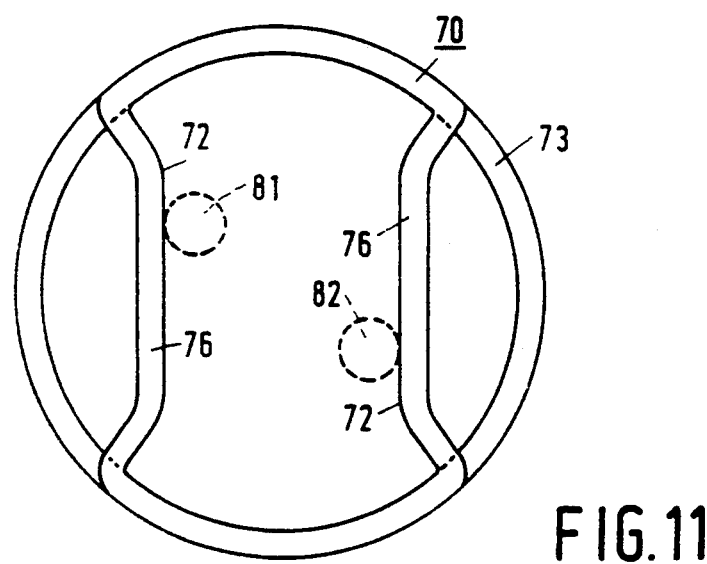
FIG. 11 shows the contact member of FIG. 10 taken on the line XI.

In FIGS. 10, 11, parts have reference numerals which are 10 higher than corresponding parts in FIGS. 8, 9.

The contact member 70 has two strips which comprise the connection areas 72. Their interspacing is smaller than the external dimension of the current supply conductor 81, 82. This conductor is brought between the strips 76 and rotated relatively until both parallel portions 81, 82 hit against a respective strip. They are then fixed.

We claim:

1. An electric lamp comprising:
  a. a lamp vessel including an enclosure portion for enclosing an electric element and at least a first end portion forming an elongate vacuum-tight seal;
  b. an electric element for effecting light emission disposed within the enclosure portion;
  c. current supply conductor means electrically connected to the electric element and extending through the first end portion;
  d. an annular insulator body disposed around an axis and having a first end attached to the elongate vacuum-tight seal and a second end extending away from said seal;
  e. a contact member for electrically connecting the lamp to a source of electric current, said contact member including:
    i. an electrically conductive contact having an accessibly-disposed face for making electrical contact with the source of electric current;
    ii. an annular rim portion extending from the contact face and disposed at least partially within the second end of the annular insulator body to support said contact face; and
    III. connection means supported by the annular rim portion for electrically connecting the contact face to the current supply conductor means.

2. An electric lamp as in claim 1 where the contact member is formed of an integral conductor.

3. An electric lamp as in claim 1 where the annular rim portion extends axially from the contact face.

4. An electric lamp as in claim 3 where the annular rim portion extends from a peripheral portion of the contact face.

5. An electric lamp as in claim 3 where the connection means comprises a conductive member extending from the annular rim portion.

6. An electric lamp as in claim 5 where the conductive member extends transversely with respect to the annular rim portion.

7. An electric lamp as in claim 3 where the connection means comprises a conductive member extending from the annular rim portion, said conductive member having an axially-extending end portion to which the current supply conductor means is attached.

8. An electric lamp as in claim 3 where the connection means comprises an extension portion of the annular rim portion which is bent inwardly toward the axis.

9. An electric lamp as in claim 1, 7 or 8 where the current supply conductor means comprises a wire bent into a U-shape.

10. An electric lamp as in claim 1, 7 or 8 where the current supply conductor means comprises first and second parallel wire segments.

11. An electric lamp comprising:
  a. a lamp vessel including an enclosure portion for enclosing an electric element and first and second pinched portions forming respective vacuum-tight seals;
  b. an electric element for effecting light emission disposed within the enclosure portion;
  c. first and second current supply conductor means electrically connected to the electric element and extending through respective ones of the first and second pinched portions;
  d. first and second annular insulator bodies disposed around respective axes and each having a first end attached to a respective one of the first and second pinched portions and a second end extending away from the respective pinched portion;
  e. first and second contact members for electrically connecting the lamp to respective sources of electric current, each of said contact members including:
    i. an electrically conductive contact having an accessibly-disposed face for making electrical contact with the respective source of electric current;
    ii. an annular rim portion extending from the respective contact face and disposed at least partially within the second end of a respective one of the first and second annular insulator bodies to support said contact face; and
    iii. connection means supported by the respective annular rim portion for electrically connecting the contact face to the current supply conductor means.

12. An electric lamp as in claim 11 where each of the first and second contact members is formed of an integral conductor.

13. An electric lamp as in claim 11 where the annular rim portion of each of the first and second contact members extends axially from the respective contact face.

14. An electric lamp as in claim 13 where each said annular rim portion extends from a peripheral portion of the respective contact face.

15. An electric lamp as in claim 13 where the connection means for each of the first and second contact members comprises a conductive member extending from the respective annular rim portion.

16. An electric lamp as in claim 15 where each said conductive member extends transversely with respect to the respective annular rim portion.

17. An electric lamp as in claim 13 where the connection means for each of the first and second contact members comprises a conductive member extending from the respective annular rim portion, said conductive member having an axially-extending end portion to which one of the current supply conductor means is attached.

18. An electric lamp as in claim 13 where the connection means for each of the first and second contact members comprises an extension of the respective annular rim portion which is bent inwardly toward the respective axis.

19. An electric lamp as in claim 11, 17 or 18 where at least one of the current supply conductor means comprises a wire bent into a U-shape.

20. An electric lamp as in claim 11, 17 or 18 where at least one of the current supply conductor means comprises first and second parallel wire segments.

* * * * *